(12) United States Patent
Regnier et al.

(10) Patent No.: US 12,126,281 B2
(45) Date of Patent: Oct. 22, 2024

(54) PENDULAR UNIT WITH AN INERTIAL MASS MOUNTED ON A PIEZOELECTRIC BEAM, IN PARTICULAR FOR AN ENERGY HARVESTER IN A LEADLESS AUTONOMOUS CARDIAC CAPSULE

(71) Applicant: CAIRDAC, Antony (FR)

(72) Inventors: Willy Regnier, Longjumeau (FR); An Nguyen-Dinh, La Riche (FR); Julien Dohin, Vanves (FR)

(73) Assignee: CAIRDAC, Antony (FR)

( * ) Notice: Subject to any disclaimer, the term of this patent is extended or adjusted under 35 U.S.C. 154(b) by 0 days.

(21) Appl. No.: 18/355,132

(22) Filed: Jul. 19, 2023

(65) Prior Publication Data
US 2024/0106356 A1 Mar. 28, 2024

(30) Foreign Application Priority Data
Sep. 27, 2022 (EP) .................... 22315218

(51) Int. Cl.
| | |
|---|---|
| H02N 2/18 | (2006.01) |
| A61N 1/362 | (2006.01) |
| A61N 1/375 | (2006.01) |
| A61N 1/378 | (2006.01) |

(52) U.S. Cl.
CPC .......... *H02N 2/186* (2013.01); *A61N 1/3785* (2013.01); *A61N 1/362* (2013.01); *A61N 1/37518* (2017.08)

(58) Field of Classification Search
CPC .. A61N 1/37518; A61N 1/3756; A61N 1/362; A61N 1/3785; A61B 5/6882; A61B 5/6869; A61B 5/6861; A61B 5/686; A61B 5/29; A61B 5/076; A61B 2560/0219; H10N 30/306; H02N 2/186; H02N 2/22
See application file for complete search history.

(56) References Cited

U.S. PATENT DOCUMENTS

| | | | | |
|---|---|---|---|---|
| 10,821,291 | B2 * | 11/2020 | Bonnet | ................. H02N 2/186 |
| 2009/0174289 | A1 | 7/2009 | Tanner | |
| 2018/0185638 | A1 * | 7/2018 | Regnier | ............... A61N 1/3756 |
| 2020/0391038 | A1 * | 12/2020 | Bonnet | ............. A61N 1/37512 |
| 2023/0369994 | A1 * | 11/2023 | Regnier | ............... A61N 1/3756 |
| 2024/0120856 | A1 * | 4/2024 | Regnier | ................. H02N 2/181 |

FOREIGN PATENT DOCUMENTS

| | | |
|---|---|---|
| CN | 104393787 A | 3/2015 |
| CN | 107355332 A | 11/2017 |
| CN | 108649837 B | 3/2021 |
| CN | 112187102 | 10/2021 |

OTHER PUBLICATIONS

European Patent Office, European Search Report issued in corresponding Application No. 22315218.2, mailed Mar. 29, 2023.

* cited by examiner

*Primary Examiner* — J. San Martin
(74) *Attorney, Agent, or Firm* — Stites & Harbison, PLLC; Jeffrey A. Haeberlin

(57) ABSTRACT

The pendular unit comprises a piezoelectric transducer beam, and an inertial mass mounted at the free distal end of the beam and comprising two half-masses arranged on either side of the beam. A mechanical connection connects the two half-masses to each other on either side of the beam in such a way as to clamp the beam between the two half-masses to secure the inertial mass to the beam, the assembly being devoid of glue between the half-masses and the beam.

10 Claims, 10 Drawing Sheets

PENDULAR UNIT WITH AN INERTIAL MASS MOUNTED ON A PIEZOELECTRIC BEAM, IN PARTICULAR FOR AN ENERGY HARVESTER IN A LEADLESS AUTONOMOUS CARDIAC CAPSULE

BACKGROUND OF THE INVENTION

Technical Field

The invention relates to energy harvesting devices, also called "harvesters" or "scavengers", which collect the mechanical energy resulting from various movements they undergo and convert this mechanical energy into electrical energy.

It more particularly relates to the harvesting devices of the so-called "PEH" (Piezoelectric Energy Harvester) type, which use as a mechanical-electrical transducer an oscillating piezoelectric beam coupled to an inertial mobile mass.

The invention will be more particularly described in an application of such energy harvesters to autonomous medical devices, in particular devices of the autonomous implantable capsule type, in particular those which are intended to be implanted in a heart cavity.

This application, although being particularly advantageous, must however not be considered as limiting the invention, whose teachings can be applied to many other types of autonomous devices incorporating an energy harvester of the PEH type, whether these devices are implantable or not, medical or not.

State of the Art

In the field of medical implants, the recent advances in miniaturization of active devices and the advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

When applied to the field of medical implants, the invention more particularly relates to those devices which incorporate a self-powering system comprising a mechanical energy harvester associated with an integrated energy storage component, such as a rechargeable battery or a high-performance capacitor.

Indeed, one of the critical aspects of these miniaturized devices is the power autonomy. The life duration of such an implant being of about 8-10 years, taking into account the very small dimensions, it is not possible to use a conventional battery, even a high-density one.

The energy harvesting device addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and charging the energy storage component. This power supply system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

The invention is nevertheless not limited to a particular type of capsule, nor even of leadless implant, and is applicable as well to many other types of autonomous devices, whatever the operational purpose thereof, cardiac or other, medical or not.

In the cardiac application case, the leadless capsule continuously monitors the patient's rhythm and if necessary issues to the heart electrical pulses for pacing, resynchronization and/or defibrillation in case of rhythm disorders detected by the capsule. The capsule further comprises various electronic circuits, sensors, etc., as well as wireless communication transmission/reception means for the remote exchange of data, the whole being integrated in a body of very small size able to be implanted at sites of difficult access or leaving little available space, such as the ventricle apex, the inner wall of the atrium, etc.

WO 2019/001829 A1 (Cairdac) describes an example of such a leadless intracardial capsule.

The invention more particularly relates to capsules or similar implantable devices whose energy harvester is of the PEH type, i.e. using a piezoelectric transducer and an inertial pendular unit subjected to the external stresses described hereinabove. The inertial pendular unit comprises, within the capsule body, a mobile mass called "seismic mass" or "inertial mass", which is driven according to the movements of the capsule, permanently subjected to the various external stresses described hereinabove. After each of these stresses, the inertial mass, which is coupled to an elastically deformable element, oscillates at a natural free oscillation frequency.

The mechanical energy of the oscillation is converted into electrical energy by a mechanical-electrical transducer producing an electrical signal. This mechanical-electrical transducer may be in particular a piezoelectric transducer that is cyclically stressed in bending so as to generate within its constituent material electrical charges that are collected at the surface of the component to be used by the self-powering system of the leadless capsule. The piezoelectric transducer is most often in the form of a beam clamped at one of its ends and coupled to the inertial mass at its other end, which is free.

The transducer output electrical signal is sent to a power management circuit of the capsule, which rectifies and regulates the electrical signal to output a stabilized direct voltage or current, usable to power the various electronic circuits and sensors of the capsule, and to charge the energy storage component.

The mechanical structure of such an energy harvester of the PEH type is described in detail in particular in WO 2018/122244 A1 (Sorin CRM/Regnier).

It will be noted that the term "beam" has to be understood in its broadest sense, i.e. an elongated, thin and flat strip, it being understood that the shape of this strip is not necessarily rectangular nor its thickness constant (as in the description of the particular embodiment that will be given hereinafter). Within the meaning of the present invention, the term "beam" hence covers elements that may have a non-constant width and/or thickness in the longitudinal direction, as well as, possibly, a deformability liable to exceed a unique degree of freedom in bending.

In the PEH structures proposed up to now, for example in above-mentioned WO 2018/122244 A1, the inertial mass is consisted of two identical half-masses, arranged symmetrically on either side of piezoelectric beam. These two half-masses form together a truncated cone and are fastened to the free end of the beam, on either side of the latter, by bonding.

The conicity of the inertial mass outer surface makes it possible to optimize the available space before entering into contact with the inside of the tube that contains the PEH. This geometry is however not exhaustive and may be adapted to its environment to optimize the mass/bulk ratio.

The material used for the inertial mass is a metal, generally a molded tungsten, that has a high density for a controlled cost price, and the size of the seismic mass is adjusted as a function of the final weight required for the desired vibratory mode, taking into account the piezoelectric beam geometry and elasticity.

The problem of the invention finds its source in the difficulties encountered due to the way the inertial mass is assembled to the piezoelectric beam, by bonding of the metal of each of the half-masses to the faces of the ceramic piezoelectric beam.

First, the presence of a chemical binding material at the metal/ceramic interface has an impact on the lifetime of the PEH. Even with a perfect control of the glues and implementation thereof, it has not been possible up to now to guarantee more than 10 years lifetime without risk of failure.

This 10-year figure (corresponding to about 30 millions of cardiac cycles) is that usually retained for the conventional cardiac pacemakers, the generator of which has anyway to be replaced at this deadline taking into account the depletion of the built-in power battery; on the other hand, in the case of a leadless pacemaker, which is difficult to explant to be replaced by a new device, the guarantee of a far longer lifetime would be needed, typically 20 years of continuous operation without failure.

However, the glues used up to now do not allow guaranteeing such a performance, even for those which degrade only slightly over time.

A second problem lies in the difficulty to correctly control the bonding process at the time of manufacturing the PEH. This process is in itself very delicate to implement due to the very reduced sizes of the parts, the necessity to operate under controlled atmosphere and to avoid any chemical pollution by contaminants liable to modify the ageing resistance properties of the bonding performed.

A third problem lies, during this bonding process, in the particular difficulty of perfectly controlling the amount of glue used: an insufficient quantity of glue obviously reduces the solidity of the final bonding obtained, but, conversely, an excess of glue results in glue effusion beyond the metal/ceramic interface, with a risk of altering the flexibility of the piezoelectric beam (which looses its flexibility at the place where the glue has spilled) with an increase of the natural vibration frequency of the pendular unit, and consequently a disruption of the system inducing a lower energy harvesting by the PEH, all things being equal otherwise.

CN 104 393 787 A proposes a pendular system with a piezoelectric beam clamped between two half-masses secured to each other by a screw-nut system. However, this method of assembly is subject to inevitable weakening, or even loosening, of the screw connection, given the permanent vibratory stresses undergone by the latter. Moreover, it does not allow precise centering of the half-masses with respect to the beam at the time of assembling the half-masses to the beam, which is a guarantee of control of the PEH vibratory characteristics, and consequently optimization of the energy harvesting function.

The purpose of the invention is to propose a new PEH module structure, and a new method for assembling such a structure, which overcomes the just-exposed difficulties and limitations, by making it possible in particular to:
  guarantee the PEH a life duration liable to reach 20 years;
  offer a simplified, economical and non-operator-dependent assembly technique; and
  obtain a PEH with perfectly controlled vibratory characteristics, and that way an optimized efficiency of the energy harvesting function.

SUMMARY OF THE INVENTION

To solve these problems and achieve the above-mentioned objects, the invention proposes a pendular unit for a PEH module, this pendular unit comprising, in a manner known per se, in particular from above-mentioned WO 2018/122244 A1, a piezoelectric transducer beam, the piezoelectric beam extending axially between a proximal end, clamped into a clamping part, and a free distal end that is elastically deformable in bending, and an inertial mass, that is mounted at the free distal end of the piezoelectric beam and mobile in transverse direction, the inertial mass comprising two half-masses arranged on either side of the piezoelectric beam at the free distal end of the latter. This pendular unit is adapted to convert a mechanical energy produced by oscillations of the pendular unit under the effect of external stresses undergone by the module into an oscillating electrical signal collected by surface electrodes of piezoelectric beam.

The pendular unit comprises a mechanical connection of the two half-masses to each other on either side of the piezoelectric beam, the mechanical connection being adapted to clamp the piezoelectric beam between the two half-masses to secure the inertial mass to the piezoelectric beam, the assembly being devoid of glue between the half-masses and the piezoelectric beam.

Characteristically of the invention, the mechanical connection of the two half-masses to each other on either side of the piezoelectric beam comprises at least one added transverse bridging part, welded to each of the two half-masses, and/or respective complementary and conjugated interlocking shapes of the two half-masses. Moreover, the piezoelectric beam comprises an orifice and/or a notch adapted to be passed through by the at least one added transverse bridging part or, respectively, by a protrusion of the complementary and conjugated interlocking shapes.

The at least one added transverse bridging part is advantageously arranged at the distal and/or proximal end of the two half-masses, and/or in a central area of the two half-masses. The respective complementary and conjugated interlocking shapes are advantageously welded together.

The invention has also for object a method for assembling such a pendular unit, comprising the following steps:
  a) obtaining a piezoelectric beam;
  b) positioning at the free distal end of the piezoelectric beam two half-masses forming the inertial mass, on either side of the piezoelectric beam; and
  c) creating a mechanical connection of the two half-masses to each other on either side of the piezoelectric beam, without addition of glue between the piezoelectric beam and the half-masses, the mechanical connection being adapted to clamp the piezoelectric beam between the two half-masses to secure the inertial mass to the piezoelectric beam, characteristically of the invention, step c) comprises:
  c1) positioning at least one transverse bridging part at the distal and/or proximal end of the two half-masses; and
  c2) welding the at least one transverse bridging part to each of the two half-masses,
and/or:
  c3) assembling the two half-masses by respective complementary and conjugated interlocking shapes; and
  c4) permanently securing the two half-masses to each other using the respective complementary and conjugated interlocking shapes.

Moreover, the piezoelectric beam comprises an orifice and/or a notch adapted to be passed through: at step c1), by the at least one added transverse bridging part or, respectively, at step c4), by a protrusion of the complementary and conjugated shapes of the two half-masses.

Step c4) advantageously comprises the welding to each other of the two respective complementary and conjugated interlocking shapes.

When the two half-masses comprise said respective complementary and conjugated interlocking shapes, step c4) advantageously comprises: c4.1) heat deforming one of the two half-masses; c4.2) interlocking the two half-masses into each other; and c4.3) letting them back to room temperature, to secure the two interlocked half-masses together by negative clearance.

The invention also encompasses a PEH comprising an elongated envelope tube and, contained inside the tube, a pendular unit as hereinabove.

The invention also encompasses an autonomous device incorporating in a device body a PEH module as hereinabove, and comprising:
  an electronic unit;
  a PEH module as hereinabove, outputting an electric signal;
  a power management circuit, adapted to rectify and regulate the electric signal produced by the PEH module, to output a stabilized direct power voltage or current; and
  an energy storage component for powering the electronic unit.

Said stabilized direct voltage or current provided by the power management circuit is used to power the electronic unit and/or to charge the energy storage component of the autonomous device.

In particular, this autonomous device can be an active medical device of the leadless capsule type, comprising a capsule body with an element for its anchoring to a wall of a patient's organ, and wherein the external stresses to which is subjected the pendular unit of the PEH module are stresses applied to the capsule body under the effect of movements of said wall and/or flow rate variations of a flow in the surrounding environment.

BRIEF DESCRIPTION OF THE DRAWINGS

An exemplary embodiment of the present invention will now be described with reference to the appended drawings, in which the same references denote identical or functionally similar elements throughout the figures.

DETAILED DESCRIPTION OF PREFERENTIAL EMBODIMENTS OF THE INVENTION

An exemplary embodiment of the device of the invention will now be described, in an application to an autonomous implantable capsule intended to be implanted into a heart cavity.

As indicated hereinabove, this particular application is given only as an example of embodiment and does not limit the invention, whose teachings can be applied to many other types of autonomous devices incorporating an energy harvester of the PEH type, whether these devices are implantable or not, medical or not.

Figure 1:
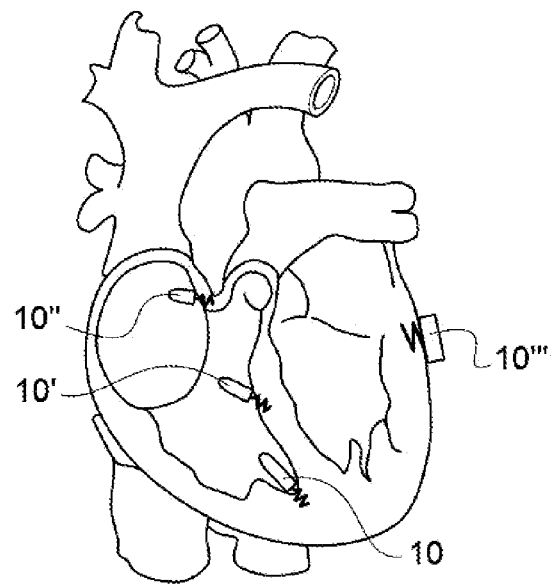
FIG. 1 illustrates medical devices of the leadless capsule type in their environment, with various examples of implantation sites in, on or near a patient's heart.

FIG. 1 shows various possibilities of implantation sites for a leadless type device in an application to cardiac pacing. Therefore, the capsule 10 is implanted inside a cavity of the myocardium (endocavitary implant), for example at the apex of the right ventricle. As an alternative, the capsule may also be implanted on the right interventricular septum, as in 10', or also on an atrial wall, as illustrated in 10". The device may also be an epicardial capsule placed on an external region of the myocardium, as illustrated in 10'''.

In any case, the leadless capsule is attached to the heart wall by means of a protruding anchoring system intended to enter the heart tissue for the holding on the implantation site. Other anchoring systems can be used, and do not change in any way the implementation of the present invention. Capsule 10 has the external form of an implant with an elongated tubular body 12 enclosing the various electronic and power supply circuits of the capsule, as well as an energy harvester with a pendular unit. The typical size of the known capsules is about 6 mm diameter for about 25 to 40 mm length.

Tubular body 12 has, at its front (distal) end 14, a protruding anchoring element, for example a helical screw 16, to hold the capsule on the implantation site. Other anchoring systems can be used, and do not change in any way the implementation of the present invention. The opposite (proximal) end 18 of capsule 10 is a free end, which is only provided with means (not shown) for the temporary connection to a guide-catheter or another implantation accessory used for implantation or explantation of the capsule, which is then detached from the latter.

Figure 2:
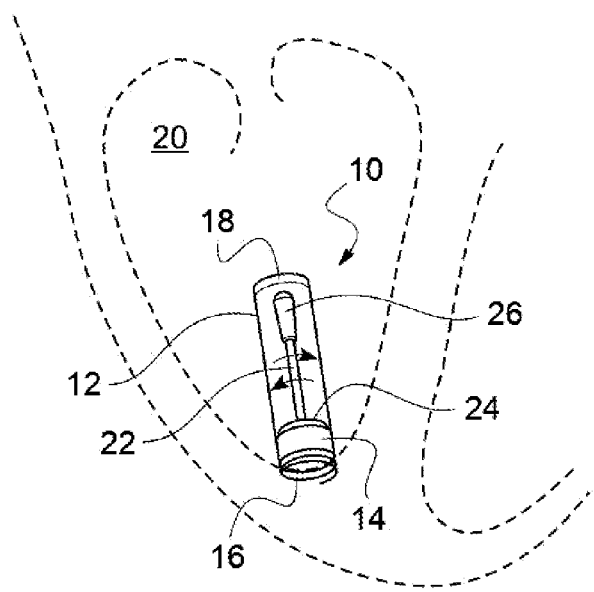
FIG. 2 illustrates a leadless capsule implanted in the bottom of the right ventricle of a patient.

In the example illustrated in FIG. 2, leadless capsule 10 is an endocavitary implant implanted into a cavity 20 of the myocardium, for example at the apex of the right ventricle. As an alternative, still in an application to cardiac pacing, the capsule can also be implanted on the interventricular septum or on an atrial wall, or also be an epicardial capsule placed on an external region of the myocardium, these different implantation modes not changing in any way the implementation of the present invention. To perform the detection/pacing functions, an electrode (not shown) in contact with the heart tissue at the implantation site collects the heart depolarization potentials and/or applies pacing pulses. In certain embodiments, the function of this electrode can be provided by anchoring screw 16, which is then an active screw, electrically conductive and connected to the detection/pacing circuit of the capsule.

Leadless capsule 10 is moreover provided with an energy harvesting module, called "PEH", comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues.

Figure 3:
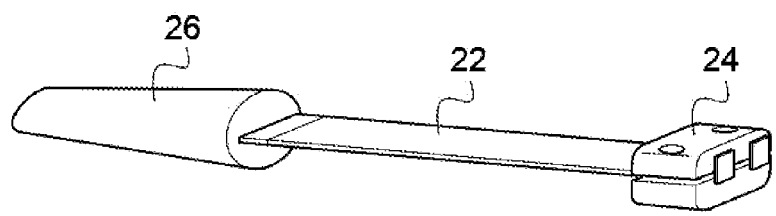
FIG. 3 shows in isolation a pendular unit of a known type, with a piezoelectric element in the form of an elongated beam clamped at one end and supporting an inertial mass at its opposite end.

The pendular unit, illustrated in isolation in FIG. 3, is consisted by a piezoelectric beam 22 secured to a clamping part 24 at one of its ends (hereinafter the "proximal end" of the beam), and whose opposite, free end (hereinafter the "distal end" of the beam) is coupled to a mobile inertial mass 26. Piezoelectric beam 22 is an elastically deformable flexible beam that constitutes, with inertial mass 26, a pendular system of the mass-spring type. Due to its inertia, mass 26 subjects beam 22 to a deformation of the vibratory type on either side of a neutral or non-deformed position corresponding to a stable rest position in the absence of any stress. The typical minimum size of the piezoelectric beams of the known devices of this type is of the order of 25 mm long for about 5 mm width.

Actually, as for its mechanical behavior, this unit may be equated to a "clamped/free beam" structure, having a natural oscillation frequency, which is herein the frequency at which the mass-spring system oscillates. It will be noted that this natural oscillation frequency, typically of the order of a few tens of hertz, is noticeably higher than the frequency of the external cyclic stresses that correspond to the heartbeat frequency (at most a few hertz). Hence, at each heart contraction, the inertial mass (or other functionally similar mechanical component) will be stressed with a higher or lower amplitude, then the pendular system will oscillate several times with decreasing amplitudes (bounces characteristic of a damped periodic oscillation), and will finally stabilize up to the following heartbeat, where the stress/oscillation cycle will be comparably repeated.

Beam 22 further performs, by piezoelectric effect, a mechanical-electrical transducer function for converting into electrical charges the mechanical bending stress that is applied to it. These charges are collected by electrodes at the surface of the beam to produce an electrical signal that, after rectification, stabilization and filtering, will power the electronic circuits of the capsule.

Figure 4:
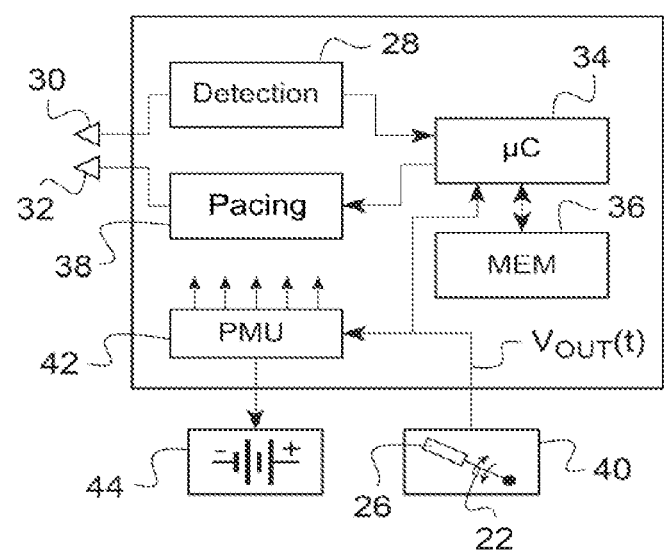
FIG. 4 schematically shows the main functional blocks of a leadless capsule.

FIG. 4 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule. Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to provide to the system of electrodes 30, 32 myocardial pacing pulses.

An energy harvesting circuit or PEH 40 is moreover provided, consisted by the pendular unit formed by piezoelectric beam 22 and inertial mass 26, described hereinabove with reference to FIGS. 2 and 3. As piezoelectric beam 22 also ensures a mechanical-electrical transducer function, it converts into electrical charges the mechanical stresses undergone and produces a variable electrical signal $V_{OUT}(t)$, which is an alternating signal oscillating at the natural oscillation frequency of the pendular beam 22/mass 26 unit, and at the rhythm of the successive beats of the myocardium to which the capsule is coupled.

The variable electrical signal $V_{OUT}(t)$ is sent to a power management circuit or PMU 42. PMU 42 rectifies and regulates the signal $V_{OUT}(t)$ so as to output a stabilized direct voltage or current for powering the various electronic circuits and charging the integrated battery 44.

On the other hand, the beam is advantageously a beam of the bimorphous type, i.e. capable of generating energy on its two faces when subjected to a deformation. Theses transduction properties are typical of a piezoelectric material, such as PZT (lead titanium-zirconate) ceramics or PMN-PT (barium titanate or lithium niobate) mono-crystals.

Figure 5:
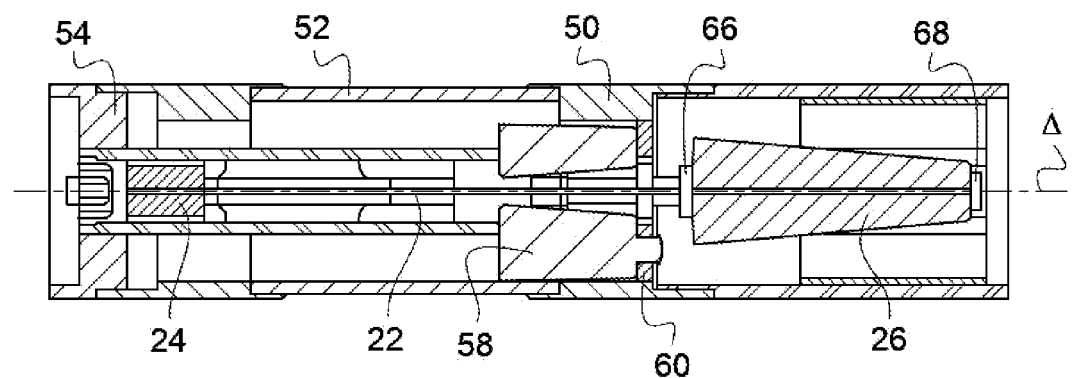
FIG. 5 is a cross-sectional view, along an axial plane, of the PEH module according to the invention.
Figure 6:
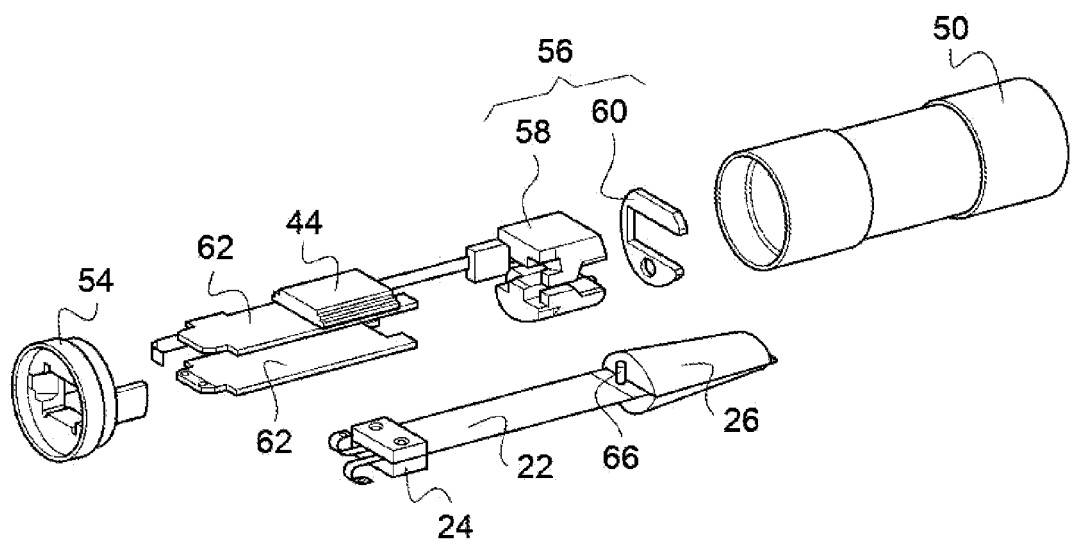
FIG. 6 is an exploded perspective view showing the different elements of the PEH module of FIG. 5.

In FIGS. 5 and 6 are shown the main elements of a PEH module according to the invention.

These different elements are contained inside an envelope tube 50, that is generally a metal tube (to allow welding operations that will be described hereinafter), preferably made of titanium due to the excellent biocompatibility of this metal.

An envelope tube particularly suitable for making a leadless capsule is described in particular in the EP 3 730 185 A1 (Cairdac), corresponding to US 2020/338241 A1 (Regnier et al.), that illustrates in particular a metal/ceramic composite tube having a central portion (52 in FIG. 5) made of a radio-frequency transparent ceramic material, in such a way as to allow a wireless communication between electronic circuits located inside the tube and the outer environment, the rest of the tube being made of a metal material such as titanium, the whole forming a one-piece tubular unit.

Envelop tube 50 contains the pendular unit consisted of beam 22 held on the proximal side by clamping part 24 and carrying inertial mass 26 on the distal side. The pendular unit is placed at the center of envelope tube 50 and aligned on axis Δ of the tube.

In the following, it will be understood by "axial direction", the direction of greater length of the beam, and by "transverse direction", the direction of deformation of the beam, a direction that is located in a radial plane and that is perpendicular to the axial direction A; the direction perpendicular to the axial and transverse directions will be called "lateral direction".

Clamping part 24 is held in the tube by a mount 54 secured to the tube, in particular a mount made of a metal material such as titanium, capable of being peripherally welded to the tube in such a way as to secure mount 54, and hence clamp 24 and beam 22, to tube 50.

EP 3 892 325 A1 (Cairdac), corresponding to US 2021/316148 A1 (Regnier et al.), describes in detail an example of clamping part and mount, and reference can be made to this document for more details.

Tube 50 also contains one or several printed circuit boards (PCBs) 62, in the example illustrated two PCBs 62, one of which carries battery 44. These two PCBs are connected to each other by a sheet of flexible conductors and supported at each of their ends, on distal side by insert 56 and on proximal side by mount 54, respectively.

The configuration of these PCBs on either side of beam 22, and the way they are connected by a flexible sheet and supported between a proximal element and a distal element are described in particular in the above-mentioned US 2019/381325 A1, to which reference can be made for more details.

Insert 56 is for example a symmetrization insert as that described in copending application U.S. Ser. No. 18/151,579 of Jan. 9, 2023, in the name of the applicant of the present application, for a "Piezoelectric energy harvester with a controlled-deflection beam, in particular for powering a leadless autonomous cardiac capsule", which is incorporated by reference. This symmetrization insert makes it possible to preserve the maximum oscillation amplitude of the beam by avoiding it to be reduced by a sub-optimal positioning of the pendular unit in the body of the module, in particular due to an imperfect positioning (off-centering, misalignment) of inertial mass 26.

The invention more particularly relates to the way the just-described inertial mass 26 of the leadless capsule pendular unit is made and assembled. FIGS. 7 to 16 illustrate various embodiments according to the invention, and FIGS. 17 to 20 illustrate the method of making a leadless capsule provided with such a pendular unit.

Inertial mass 26 comprises, in a manner known per se, two half-masses 64, 64, generally frustoconical in shape, arranged on either side of piezoelectric beam 22 at the free distal end of the latter.

Characteristically of the invention, it is provided a mechanical connection of the two half-masses 64, 64, to each other on either side of piezoelectric beam 22.

This piezoelectric connection between the two half-masses 64, 64 is designed to clamp piezoelectric beam 22 between the two half-masses 64, 64, in such a way as to secure the whole without the presence of glue at the metal half-mass/ceramic piezoelectric beam interface.

Figure 7:
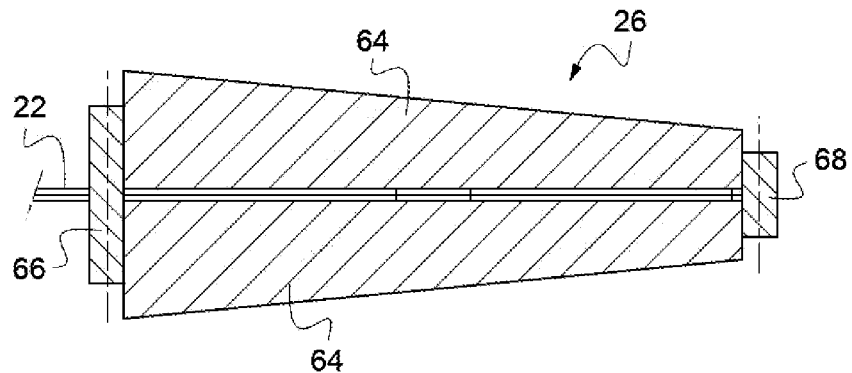
FIG. 7 is a cross-sectional view, along an axial plane, of an inertial mass of a pendular unit according to a first embodiment of the invention.
Figure 8:
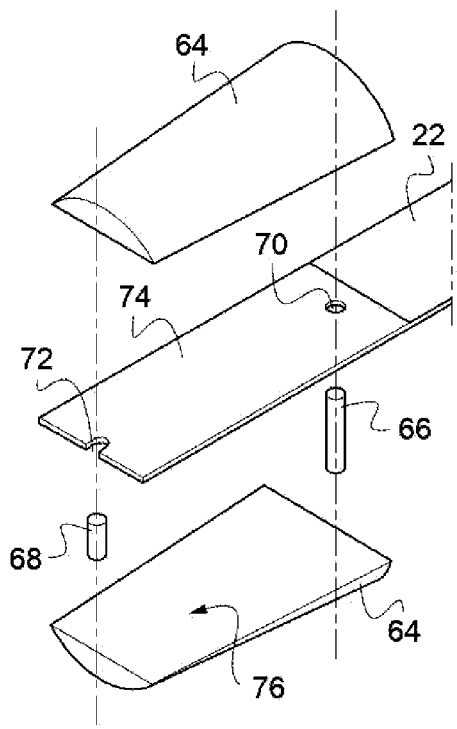
FIGS. 8 and 9 are exploded and assembled perspective views, respectively, of the inertial mass of the pendular unit illustrated in FIG. 7.
Figure 9:
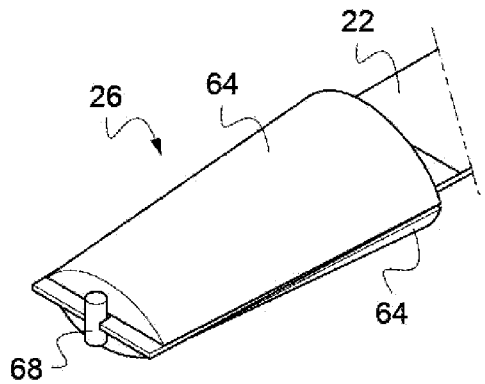

FIGS. 7 to 9 illustrate a first embodiment of this mechanical connection according to the invention.

The two half-masses 64, 64 are joined together by two transverse bridging parts 66, 68 arranged at the proximal and the distal end, respectively, of the half-masses.

These bridging parts are for example respective metal shafts or rods passing through a hole or a notch 70, 72 of piezoelectric beam 22, made in an end region 74 of the piezoelectric beam that is devoid of surface electrodes or, as an alternative, by adding an isolating element. This avoids that, with a bridging part 66 or 68 made of an electrically conductive material, this part short-circuits electrodes of the piezoelectric beam, thereby canceling the positive and negative charges generated on either side of the piezoelectric beam. On the other hand, half-masses 64, 64 have, on their side turned towards piezoelectric beam 22, a flat face 76 adapted to be applied against end region 74 of this piezoelectric beam.

Bridging parts 66, 68 are made of a material suitable to be welded to each of the ends of half-masses 64, 64, for example 316L stainless steel, or preferably, tungsten, when half-masses 64 are also made of tungsten.

In this embodiment, the mechanical connection of the two half-masses to each other is made by: centering half-masses 64, 64 against piezoelectric beam 22; pressing (clamping) the half-masses against the piezoelectric beam; positioning bridging parts 66, 68 at the respectively proximal and distal ends of each of the half-masses; finally, welding the bridging parts to the half-masses.

Once this welding performed, piezoelectric beam 22 remains tightened and clamped between the two half-masses 64, 64 and permanently secured to the latter, the final configuration obtained being that illustrated in FIG. 9.

Figure 10:
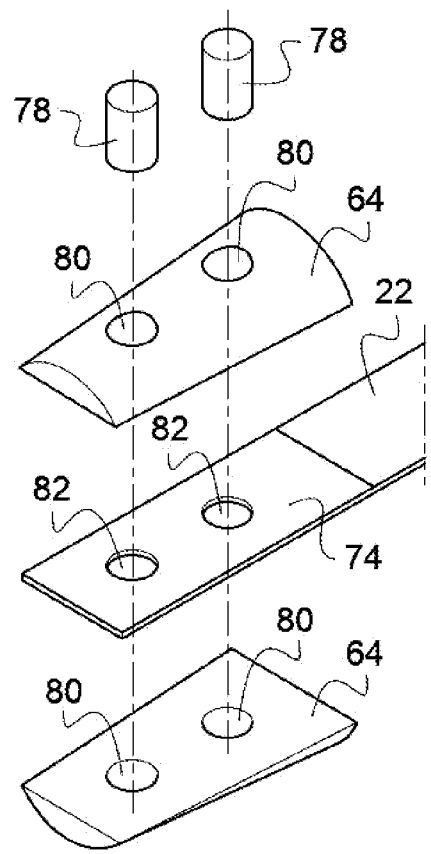
FIGS. 10 and 11 are exploded and assembled perspective views, respectively, of an inertial mass of a pendular unit according to a second embodiment of the invention.
Figure 11:
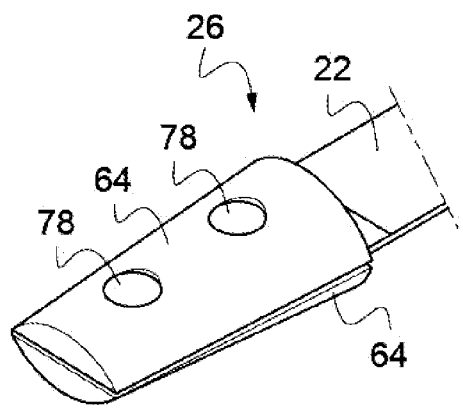

FIGS. 10 and 11 illustrate a second embodiment, which is an alternative to the previous one.

In this second embodiment, the bridging parts are transverse shafts 78 that are inserted into corresponding bores 80 of half-passes 64, 64 and that pass through orifices 82, 82 made in a central area of piezoelectric beam 22 (instead of a peripheral area as in the first embodiment), in the electrodeless area 74.

Shafts 78 are preferably made of a metal material, very preferentially tungsten, just as half-masses 64, to benefit from the very high density of this metal. As an alternative, the central shafts 78 may also be made of a synthetic material, for example PEEK (polyetheretherketone) or another synthetic material.

When shafts 78 are made of metal, the mechanical connection of shafts 78 to half-masses 64 is advantageously a welded connection, as in the first embodiment; as an alternative, this connection may also be a bonded connection, in particular in the case of bridging parts 78 made of synthetic material (it will be noted that, in this embodiment, the bonding is made between bridging parts 78 and half-masses 64 but that there is no bonding of these half-masses to piezoelectric beam 22).

Figure 12:
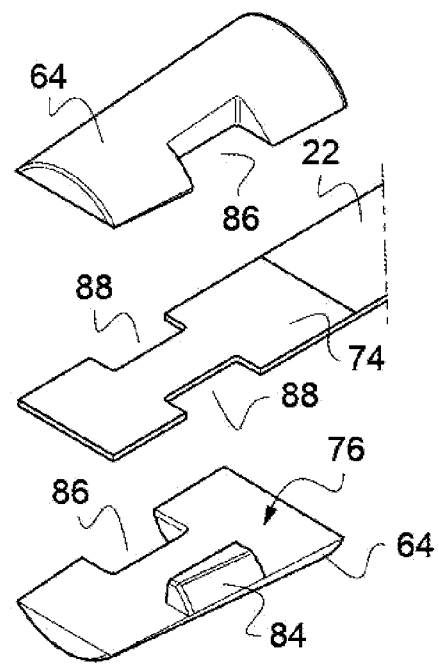
FIGS. 12 and 13 are exploded and assembled perspective views, respectively, of an inertial mass of a pendular unit according to a third embodiment of the invention.
Figure 13:
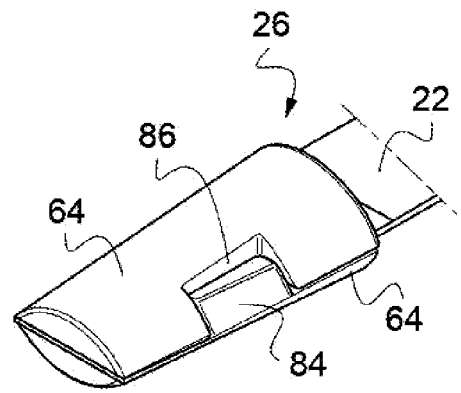

FIGS. 12 and 13 illustrate a third embodiment of the invention that does not require the use of an added element to make the mechanical connection of the two half-masses to each other, unlike the bridging parts of the two preceding embodiments.

In this third embodiment, the half-masses are made as two identical interlocking parts, mounted opposite each other on either side of piezoelectric beam 22. More precisely, each of the half-masses 64 has, on the side of flat face 76 intended to come into contact with piezoelectric beam 22, a protrusion 84 adapted to interlock into an indentation of conjugated shape 86 of the opposite half-mass located on the other side of piezoelectric beam 22. This opposite half-mass also comprises a protrusion adapted to interlock into an indentation 86 of the first half-mass. Piezoelectric beam 22 has two notches 88 at the location of protrusions 84.

It should be noted in this respect that the interlocking half-masses 64 are not necessarily identical; on the contrary, to make the assembly easier, it may be advantageous to provide different positions and sizes for the protrusions 48 and conjugated indentations 86 on the two half-masses 64.

This embodiment has also for advantage to allow, thanks to the conjugated shapes of the protrusions 84 and indentations 86, a simple assembly and centering of the two half-masses on piezoelectric beam 22.

Once the two half-masses joined together, the unit has the configuration illustrated in FIG. 13 and the permanent securing of the two half-masses to each other can be obtained by one or several welding points, in particular at the protrusion 84/indentation 86 interfaces. In an weldless alternative, after having heat deformed one of the two interlocking parts, the two interlocking parts are joined together then the unit is let back to room temperature to secure the two interlocked half-masses together by negative clearance.

Figure 14:
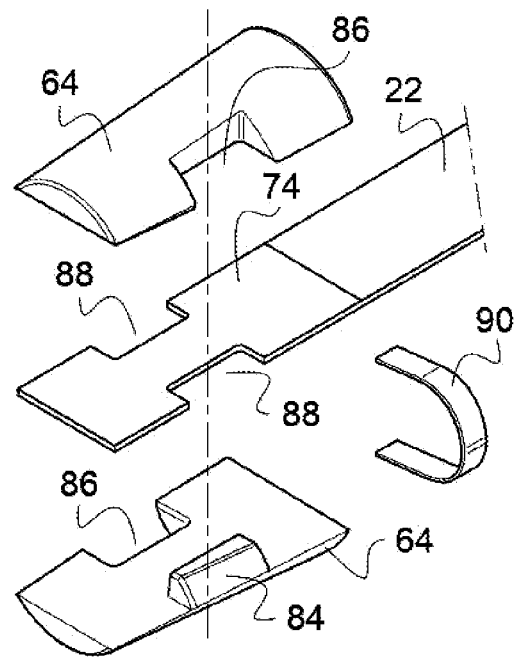
FIGS. 14 and 15 are exploded and assembled perspective views, respectively, of an inertial mass of a pendular unit according to a fourth embodiment of the invention.
Figure 15:
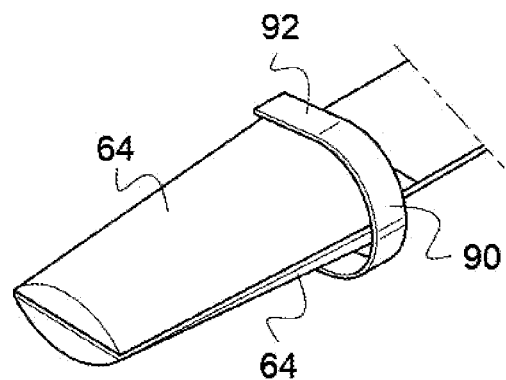
Figure 16:
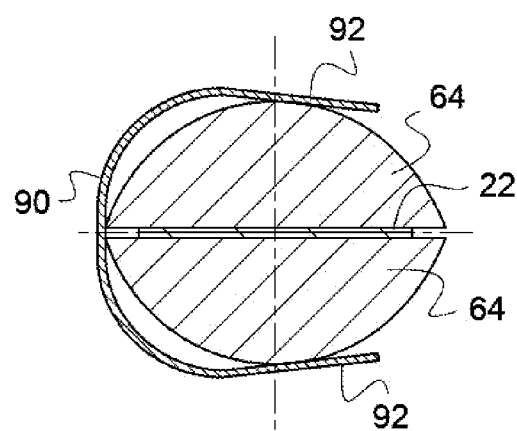
FIG. 16 is a cross-sectional view, along a radial plane, of the inertial mass of the pendular unit illustrated in FIGS. 14 and 15.

FIGS. 14 to 16 illustrate a fourth embodiment of the invention, which is an alternative to the preceding one.

In this embodiment, to avoid having to weld or heat deform the two half-masses, a strapping part or shrink ring 90 is inserted, which surrounds all or part of the two half-masses after assembly of these latter on either side of piezoelectric beam 22. Strapping part 90 comprises bearing faces 92 that press the two half-masses 64 against each other, with a controlled forced, preferably lower than 10 N. Strapping part 90 can be made of a metal material (for example, stainless steel or nitinol) or a synthetic material (for example, PEEK).

Figure 17:
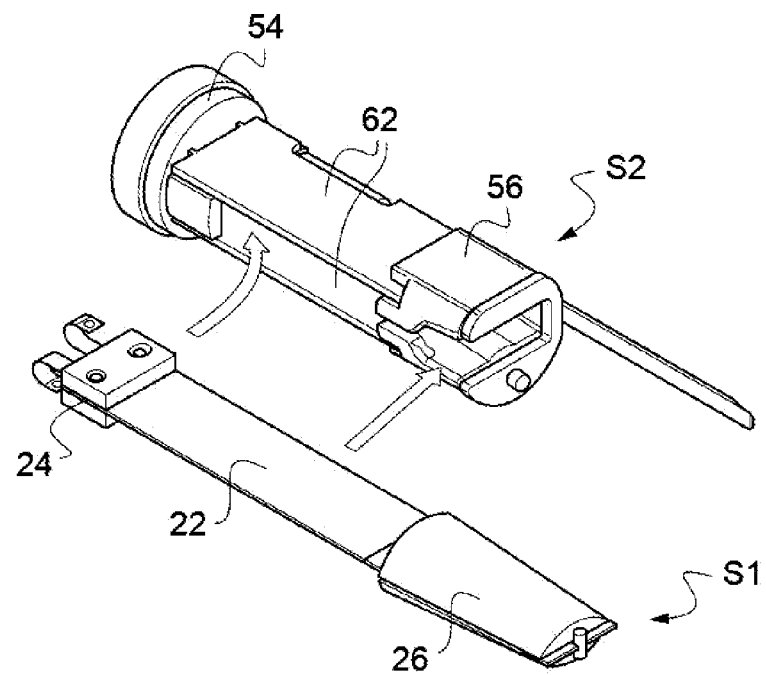
FIGS. 17 and 18 illustrate two steps of assembly of a leadless capsule with a PEH module comprising a pendular unit according to the invention.
Figure 18:
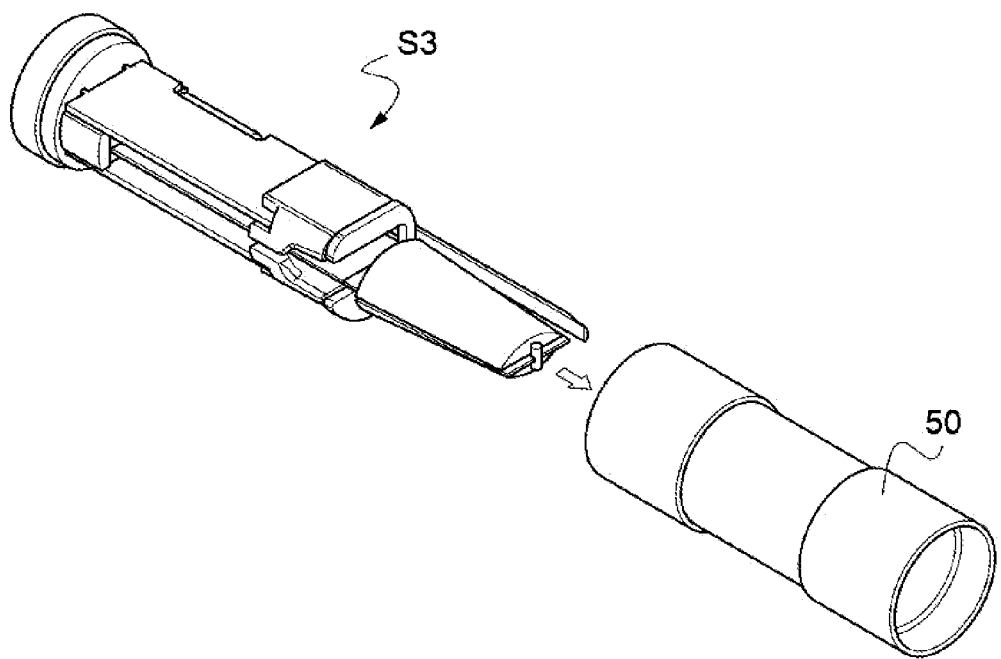
Figure 19:
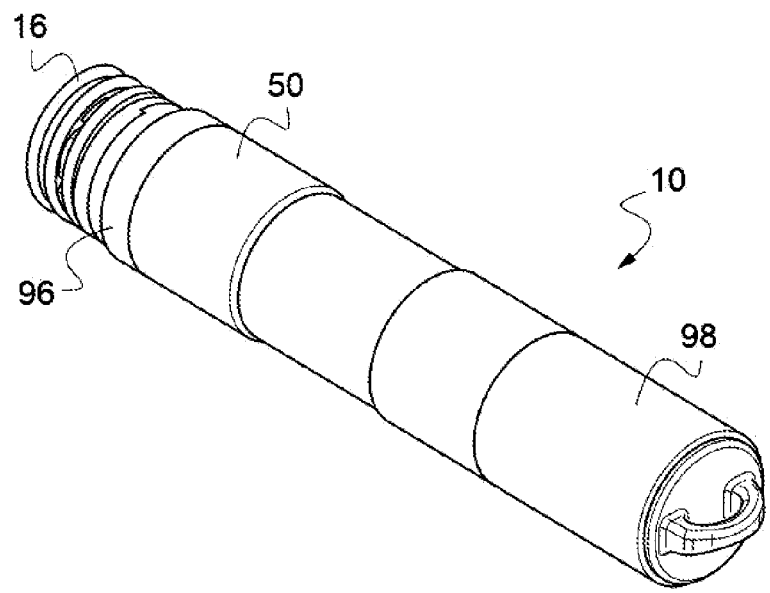
FIG. 19 illustrates the final implantable leadless capsule obtained at the end of the process.
Figure 20:
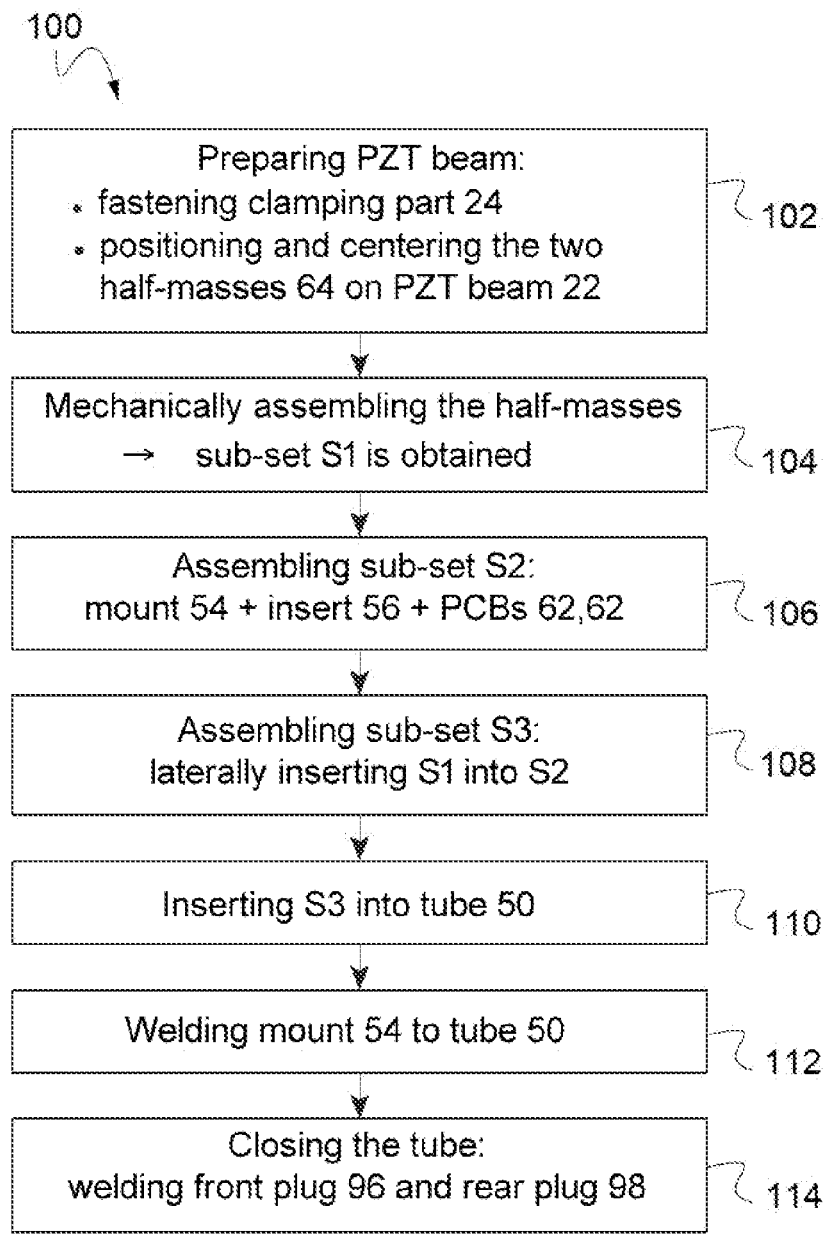
FIG. 20 is a flow diagram explaining the different steps of the process of assembling an implantable leadless capsule comprising a PEH module with a pendular unit according to the invention.

With reference to FIGS. 17 to 19 and to the flow diagram of FIG. 20 showing the different steps of the process, the way are manufactured and assembled the PEH module comprising the pendular unit provided with the just-described seismic mass, as well as the full leadless capsule integrating such a module, will now be disclosed.

The first step (block 102 of flow diagram 100 of FIG. 20) consists in preparing piezoelectric beam 22 by attaching it, at its proximal end, to clamping part 24 and by positioning and centering, at its distal end, the two half-masses 64 on either side of the beam, according to one of the above-described embodiments.

The following step (block 104) consists in making the permanent mechanical connection of the two half-masses to each other while sandwiching the piezoelectric beam. A first sub-set S1 is thus obtained (FIG. 17), which is consisted of piezoelectric beam 22 with clamping part 24 at its proximal end and inertial mass 26 at its distal end.

The following step (block 106) consists in assembling a sub-set S2 (FIG. 17) gathering mount 54 and insert 56, with the two PCBs 62 mounted between these two elements 54 and 56.

The following step (block 108) consists in gathering sub-sets S1 and S2 into one sub-set S3 (FIG. 18) by introducing sub-set S1 into the lateral space arranged between insert 56, mount 54 and the two PCBs 62 of sub-set S2.

The following step (block 110) consists in introducing this sub-set S3 into envelop tube 50 by axial translation (FIG. 18). Mount 54 is then welded to tube 50 (step 112), for example by means of peripheral laser shots.

The final step (block 114) consists in closing at its two ends the envelope tube 50 containing the pendular unit, by adding a front plug 96 carrying anchoring screw 16 of the leadless capsule and a rear plug 98. These plugs 96 and 98 are attached to tube 50 by peripheral laser weldings. The leadless capsule is then in its final assembled state, as illustrated in FIG. 19.

The invention claimed is:

1. A pendular unit for an energy harvesting module, PEH, the pendular unit comprising:
   a piezoelectric transducer beam, the piezoelectric beam extending axially between a proximal end, clamped into a clamping part, and a free distal end that is elastically deformable in bending; and
   an inertial mass, that is mounted at the free distal end of the piezoelectric beam and mobile in a transverse direction, the inertial mass comprising two half-masses arranged on either side of the piezoelectric beam at the free distal end of the piezoelectric beam,
   wherein the pendular unit is adapted to convert a mechanical energy produced by oscillations of the pendular unit under the effect of external stresses undergone by the module into an oscillating electrical signal collected by surface electrodes of the piezoelectric beam,
   wherein the pendular unit comprises a mechanical connection of the two half-masses to each other on either side of the piezoelectric beam, the mechanical connection being adapted to clamp the piezoelectric beam between the two half-masses to secure the inertial mass to the piezoelectric beam, the assembly being devoid of glue between the half-masses and the piezoelectric beam,
   wherein the mechanical connection of the two half-masses to each other on either side of the piezoelectric beam comprises at least one of:
      at least one added transverse bridging part, welded to each of the two half-masses, and
      respective complementary and conjugated interlocking shapes of the two half-masses,
   and wherein the piezoelectric beam comprises at least one of an orifice and a notch adapted to be passed through:
      by the at least one added transverse bridging part
   or, respectively,
      by a protrusion of the complementary and conjugated interlocking shapes.

2. The pendular unit of claim 1, wherein the at least one added transverse bridging part is arranged at at least one of the distal and the proximal end of the two half-masses.

3. The pendular unit of claim 1, wherein the at least one added transverse bridging part is arranged in a central area of the two half-masses.

4. The pendular unit of claim 1, further comprising at least one welding point between the respective complementary and conjugated interlocking shapes.

5. The pendular unit of claim 1, wherein the pendular unit is integrated to an energy harvesting module, PEH, comprising an elongated envelope tube containing the pendular unit.

6. The pendular unit of claim 5, wherein the PEH is integrated to an autonomous device having a device body containing:
   an electronic unit;
   a power management circuit, adapted to rectify and regulate the electric signal produced by the PEH module, to output a stabilized direct power voltage or current; and
   an energy storage component for powering the electronic unit,
   wherein said stabilized direct voltage or current provided by the power management circuit is used to power the electronic unit and/or to charge the energy storage component of the autonomous device.

7. The pendular unit of claim 6,
wherein the autonomous device is an active medical device of the implantable autonomous capsule type comprising a capsule body with an element for its anchoring to a wall of a patient's organ,
and wherein the external stresses to which is subjected the pendular unit of the PEH module are stresses applied to the capsule body under the effect of movements of said wall and/or flow rate variations of a flow in the surrounding environment.

8. A method for assembling a pendular unit for an energy harvesting module, PEH, the pendular unit comprising a piezoelectric transducer beam, that is elastically deformable in bending, and an inertial mass, that is mounted at the free distal end of the piezoelectric beam and mobile in a transverse direction,
the method comprising the following steps:
a) obtaining a piezoelectric beam;
b) positioning at the free distal end of the piezoelectric beam two half-masses forming the inertial mass, on either side of the piezoelectric beam; and
c) creating a mechanical connection of the two half-masses to each other on either side of the piezoelectric beam, without addition of glue between the piezoelectric beam and the half-masses, the mechanical connection being adapted to clamp the piezoelectric beam between the two half-masses to secure the inertial mass to the piezoelectric beam,
wherein step c) comprises at least one of:
c1) positioning at least one transverse bridging part at at least one of the distal and the proximal end of the two half-masses; and
c2) welding the at least one transverse bridging part to each of the two half-masses,
and:
c3) assembling the two half-masses by respective complementary and conjugated interlocking shapes; and
c4) permanently securing the two half-masses to each other using the respective complementary and conjugated interlocking shapes,
and wherein the piezoelectric beam comprises at least one of an orifice and a notch adapted to be passed through:
at step c1), by the at least one added transverse bridging part, or, respectively,
at step c4), by a protrusion of the complementary and conjugated shapes of the two half-masses.

9. The method of claim 8,
wherein step c4) comprises the welding to each other of the two respective complementary and conjugated interlocking shapes.

10. The method of claim 8,
wherein, the two half-masses comprising said respective complementary and conjugated interlocking shapes, step c4) comprises:
c4.1) heat deforming one of the two half-masses;
c4.2) interlocking the two half-masses into each other; and
c4.3) letting them back to room temperature, to secure the two interlocked half-masses together by a negative clearance.

* * * * *